(12) United States Patent
Otani et al.

(10) Patent No.: US 8,666,138 B2
(45) Date of Patent: Mar. 4, 2014

(54) METHODS AND SYSTEMS FOR FUNCTIONAL IMAGING OF CARDIAC TISSUE

(75) Inventors: Niels F. Otani, Ithaca, NY (US); Stefan Luther, Gottingen (DE); Robert F. Gilmour, Jr., Ithaca, NY (US); Rupinder Singh, Mountain View, CA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/393,973

(22) PCT Filed: Sep. 3, 2010

(86) PCT No.: PCT/US2010/047767
§ 371 (c)(1),
(2), (4) Date: May 16, 2012

(87) PCT Pub. No.: WO2011/028973
PCT Pub. Date: Mar. 10, 2011

(65) Prior Publication Data
US 2012/0243758 A1    Sep. 27, 2012

Related U.S. Application Data

(60) Provisional application No. 61/239,982, filed on Sep. 4, 2009.

(51) Int. Cl.
*G06K 9/00* (2006.01)
*A61N 1/00* (2006.01)

(52) U.S. Cl.
USPC .............................. 382/131; 600/16

(58) Field of Classification Search
USPC ............ 382/128–134; 600/16, 324, 374, 437, 600/438, 450, 459, 481, 483, 485, 504, 508, 600/509, 513, 514, 479; 607/13, 28, 30, 607/119, 122, 129, 902; 128/920, 922
See application file for complete search history.

(56) References Cited

U.S. PATENT DOCUMENTS

| | | | |
|---|---|---|---|
| 4,858,610 A | 8/1989 | Callaghan et al. | |
| 6,540,659 B1 * | 4/2003 | Milbocker | 600/17 |
| 6,749,571 B2 * | 6/2004 | Varghese et al. | 600/450 |
| 7,022,077 B2 * | 4/2006 | Mourad et al. | 600/449 |
| 7,349,738 B1 * | 3/2008 | Bradley et al. | 607/28 |
| 7,736,315 B2 * | 6/2010 | Vanderby et al. | 600/438 |
| 2004/0122320 A1 | 6/2004 | Murashita | |
| 2007/0049824 A1 | 3/2007 | Konofagou et al. | |
| 2009/0163806 A1 | 6/2009 | Sadamitsu et al. | |

OTHER PUBLICATIONS

International Search Report for PCT/US10/47767 dated Apr. 11, 2011.

(Continued)

*Primary Examiner* — Abolfazl Tabatabai
(74) *Attorney, Agent, or Firm* — Burns & Levinson LLP; Jacob N. Erlich; Orlando Lopez

(57) ABSTRACT

One embodiment of these teachings includes an imaging modality that is based on the ability of imaging technologies to detect wave-induced tissue deformation at depth, that allows viewing the propagation of action potentials deep within myocardial tissue, thereby helping to clarify clinical and physiological dynamical issues.

12 Claims, 5 Drawing Sheets

(56) References Cited

OTHER PUBLICATIONS

Otani, N. F. et al., Use of Ultrasound Imaging to Map Propagating Action Potential Waves in the Heart, Computers in Cardiology 2009;36:617-620 (Proceedings of conference on Sep. 13-16, 2009).

Ahn, C. Y., The Principles and Applications of the Ultrasound Diagnostic System, KSIAM 2008 Annual Meeting, Nov. 28-29, 2008 (4 pages).

Cui, Y., et al. Displacement and strain estimation of breast tissue using multicompressed ultrasound RF signals, MIAS-IRC Plenary 2005 Online Proceedings (2 pages).

* cited by examiner

METHODS AND SYSTEMS FOR FUNCTIONAL IMAGING OF CARDIAC TISSUE

CROSS REFERENCE TO RELATED APPLICATIONS

This application is the U.S. national phase entry under 35 U.S.C. §371 of International Patent Application No. PCT/US10/47767 filed Sep. 3, 2010, entitled METHODS AND SYSTEMS FOR FUNCTIONAL IMAGING OF CARDIAC TISSUE, which in turn claims priority from U.S. Provisional Application Ser. No. 61/239,982, filed Sep. 4, 2009, entitled FUNCTIONAL ULTRASOUND IMAGING OF CARDIAC TISSUE, both of which are incorporated by reference herein in their entirety for all purposes.

BACKGROUND

These teachings relate generally to imaging modalities based on the ability of imaging technologies to detect wave-induced tissue deformation.

Some cells, referred to as excitable cells, can reverse their resting membrane potential from negative values to slightly positive values. This rapid change in membrane potential is referred to as an action potential. Typically, the action potential is the result of a rapid change in membrane permeability to certain ions. Nerve cells and muscle cells are excitable cells. Heart muscle cells are excitable cells and their action potential is referred to as cardiac action potential (or simply as action potential).

Current technology does not allow us to see action potential propagation deep within the walls of the heart. This deficiency has a number of consequences. In the clinical setting, diagnostics such as the electrocardiogram (ECG) or electrophysiology (EP) studies are relied on to provide information about the heart's electrical state. While these tests do certainly yield a wealth of valuable information, they often do not provide a fundamental understanding of the dynamics underlying the patient's cardiac rhythm. For example, the field of cardiology is currently moving away from EP studies as a diagnostic for determining whether to implant an implantable cardioverter defibrillator (ICD), relying instead on the ejection fraction, paradoxically a mechanical rather than electrical measure, as the basis for the decision. This suggests that an improved diagnostic for assessing the patient's rhythm dynamics is needed. At the research level, this lack of a deep, panoramic view of action potential activity means that it can not be said with certainty that ventricular fibrillation (VF) is caused by multiple reentrant action potential waves, although of course it is strongly suspected. Even if VF is a manifestation of multiple waves, the nature of the dynamics of these waves remains controversial, with their induction and maintenance being attributed to either tissue heterogeneity or steep electrical restitution, and their spatial patterning thought to be composed of either several rotating waves on equal dynamical footing, or one dominant "mother rotor" wave driving fibrillatory conduction. The lack of clarity on these issues has greatly complicated the development of effective therapies for the prevention and treatment of several types of tachyarrhythmias, including VF.

This bewildering landscape of theoretical wave propagation patterns and the mechanisms for their initiation and maintenance are what have led researchers to develop tools that might be used to actually see what patterns exist during VF and other rapid, abnormal rhythms. Rudy et al. have developed an impressive, noninvasive method called ECGi to track action potential propagation on the epicardium using hundreds of electrodes situated on the body surface. This method does not as yet provide transmural information, however. Other approaches, such as the use of plunge electrodes, transillumination, and optical tomography can provide a 3D representation of the electrical activity in the heart. Plunge electrodes and transillumination can also capture the complex electrical dynamics of scroll waves in reentry. The spatial resolution of the plunge electrode method is, however, relatively low; furthermore, it is likely that the presence of these electrodes creates electrical heterogeneities that strongly modify the patterns of propagation. Both transillumination and optical tomography techniques have some light penetration problems, thus potentially making them difficult to apply to thicker myocardial walls such as those found in canine or human ventricles. Additionally, optical tomography cannot be applied in-vivo.

BRIEF SUMMARY

In one embodiment, the method of these teachings includes obtaining an image of at least a portion of a heart during in vivo or in vitro operation, obtaining, from the image, tissue displacement information, and obtaining, from the tissue displacement information, stresses causing the tissue displacements, whereby information on action potential inducing the stresses can be obtained.

An embodiment of the system of these teachings includes one or more processors and one or more computer usable media that has computer readable code embodied therein, the computer readable code causing the one or more processors to obtain, from an image of at least a portion of a heart during in vivo or in vitro operation, tissue displacement information, and obtaining, from the tissue displacement information, stresses caused in the tissue displacements, whereby information on action potential inducing the stresses can be obtained.

Embodiments of articles of manufacture having computer usable media on which the computer usable code is embodied therein are also within the scope of these teachings.

For a better understanding of the present teachings, together with other and further needs thereof, reference is made to the accompanying drawings and detailed description and its scope will be pointed out in the appended claims.

BRIEF DESCRIPTION OF THE DRAWINGS

FIG. 4b and FIGS. 4c-4j show the input into, and the results from, the inverse model, respectively, in various projected operating environments.

DETAILED DESCRIPTION

Figure 1:
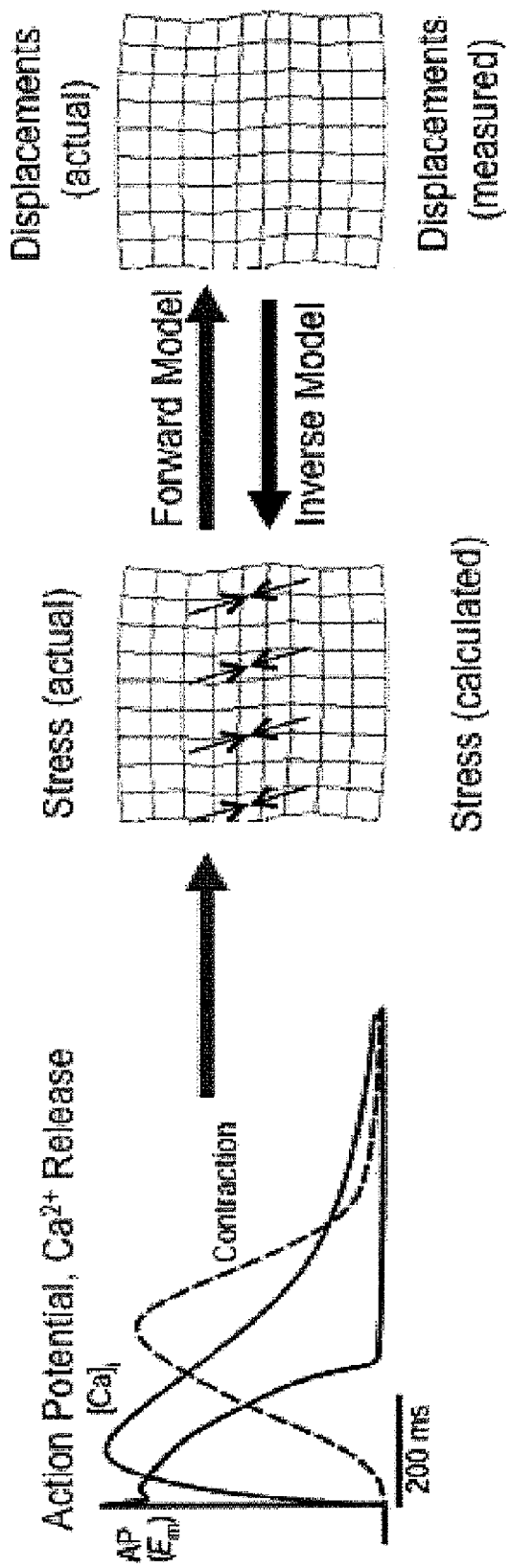
FIG. 1 shows contractions, in turn, lead in general to the deformation of the entire tissue as illustrated schematically in the right panel of the figure.

In one embodiment, the method of these teachings includes obtaining an image of at least a portion of a heart during in vivo or in vitro operation, obtaining, from the image, tissue displacement information, and obtaining, from the tissue displacement information, stresses causing the tissue displacements, whereby information on action potential inducing the stresses can be obtained. In one instance, the determination of stresses for each pixel or nodal point in a group of pixels or nodal points is obtained by operating on displacements for each pixel or nodal point in a group of pixels or nodal points rather than by operating on each pixel or nodal point separately.

One embodiment of these teachings includes a new imaging modality that is based on the ability of present day ultrasound to detect wave-induced tissue deformation at depth, that will allow the viewing of the propagation of action potentials deep within myocardial tissue, thereby helping to clarify these clinical and physiological dynamical issues. In one instance, strain information is extracted from the deformations appearing in the ultrasound images that are caused by action potential propagation activity, and these strains are converted into the action potential induced stresses that caused them. These stresses will then serve as markers for the presence of the action potentials, allowing us to creating mappings of their propagation as functions of both time and space. An ultrasound technique that can be utilized in this modality is already the subject of intense study by Konofagou and collaborators, although these teachings are not limited to only that technique. (The US patent publications, US20080097202, US20070049824, are incorporated by reference herein in their entirety and the publications, Ophir J, Alam S K, Garra B, Kallel F, Konofagou E, Krouskop T, Varghese T, Elastography: ultrasonic estimation and imaging of the elastic properties of tissues, *Proc Inst Mech Eng H.,* 1999; 213(3):203-33. Lee W-N. and Konofagou E. E., Angle-Independent and Multi-Dimensional Myocardial Elastography: From Theory to Clinical Validation, *Ultrasonics,* 48(6-7):563-7, 2008 [Invited], Wang S., Lee W-N, Provost J, Luo J. and Konofagou E. E., Composite Elasticity Imaging for the Detection of Cardiovascular Disease, *IEEE Trans. Ultras. Ferroel. Freq. Control.,* 55: 2221-2233, 2008, Lee W. N., Qian Z., Tosti C. L., Brown, T. R., Metaxas D. N. and Konofagou E. E. Validation of Angle-Independent Myocardial Elastography Using MR Tagging in Human Subjects In Vivo, *Ultras. Med. Biol.* 34(12):1980-97, 2008, Choi J. J., Wang S., Brown T. R., Duff K. E. and Konofagou E. E., Noninvasive and Transient Blood-Brain Barrier Opening in the Hippocampus of Alzheimer's Double Transgenic Mice Using Pulsed Focused Ultrasound, *Ultrasonic Imaging,* 189-200, 2008 and Luo J., Fujikura K., Tyrie L., Tilson III M. D. and Konofagou E. E., Pulse Wave Imaging of Normal and Aneurysmal Abdominal Aortas In Vivo, *IEEE Trans. Med. Imag.,* 2009 (in press), all of which are also incorporated by reference herein in their entirety.) It should be noted that the goals of Konofagou and collaborators are principally to assess the normal and pathological states of the cardiac tissue, and are quite different from the action potential mapping goals of the present teachings.

The method of these teachings provides a technique that is capable of reconstructing from the mechanical motion extracted from a series of hypothetical ultrasound images the magnitude of active stresses induced by the passage of action potentials. The locations of these active stresses as functions of time serve as reasonable markers for the locations of the action potentials themselves, thereby allowing, among other outputs, the construction of movies showing the propagation of action potentials within cardiac tissue, in two and three spatial dimensions and the use in diagnosis and therapy of the obtained data.

From the present major imaging modalities capable of 3D visualization, the 3D implementations of ultrasound are among the most promising for investigating the behavior of arrhythmias deep within cardiac tissue. Present day magnetic resonance imaging (MRI) and computed tomography (CT) are also capable of noninvasively mapping the 3D contractile motion resulting from electrical activity in the heart. Compared to these other imaging methods, present-day ultrasound imaging is attractive because of its relative ease of use, real-time feedback, portability, lack of radiation, cost effectiveness, and widespread availability. Ultrasound techniques have been demonstrated, at least in 2D, to be capable of yielding real-time, highly temporally resolved images of electromechanical wave contractions in humans. Although CT and MRI provide very high spatial resolution, neither technology, in its present-day state, has the time resolution necessary (5-10 ms) to visualize the relatively fast timescale events inherent in the propagation of action potential waves. However, these teachings do not exclude utilizing technologies other than ultrasound when, or if, those technologies develop the capability to visualize the propagation of action potential waves.

The imaging technique of these teachings is based on the fact that propagating action potentials in the heart create calcium transients within the myocytes, causing them to contract, as depicted by the left panel in FIG. 1. This active contraction occurs predominantly along the local fiber direction (arrows in the center panel), in the portion of the tissue occupied or recently occupied by the action potential. The contractions, in turn, lead in general to the deformation of the entire tissue as illustrated schematically in the right panel of FIG. 1. In one embodiment the method of these teachings extracts the tissue displacements from ultrasound images showing the tissue deformation, and converts the displacements into the action-potential-induced stresses that caused them, using a computer algorithm referred to here as the inverse model (as shown in FIG. 1).

Referring to FIG. 1, as suggested by the forward arrows, the passage of action potentials through individual cells causes time-dependent processes in these cells (left panel), which lead to local contraction of the tissue primarily in the fiber direction (arrows in the center panel), causing deformation and therefore displacement of the entire tissue (right panel). Models of both of the forward problem (the creation of displacements from known stresses) and the inverse problem (the determination of the stresses that had to be present to create a given displacement field; blue arrow) are described hereinbelow.

Figure 2:
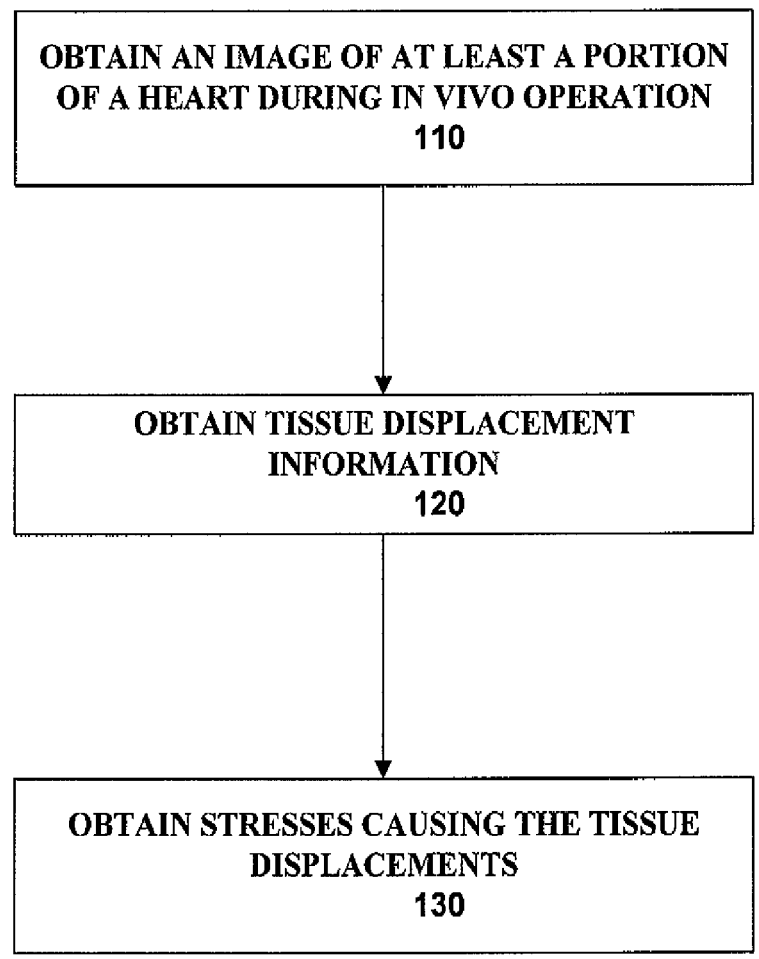
FIG. 2 is a schematic flow chart representation of an embodiment of the method of these teachings.

FIG. 2 shows a flowchart of an embodiment of the method of these teachings. Referring to FIG. 2, an image of at least a portion of a heart during in vivo or in vitro operation is obtained (step 110, FIG. 2). From the image, tissue displacement information is obtained (step 120, FIG. 2). The tissue displacement information can be inverted to obtain the stresses is causing the tissue displacement (step 130, FIG. 2). The stresses can be related to the action potentially induced contractions, from which the action potentials can be inferred.

Figure 3:
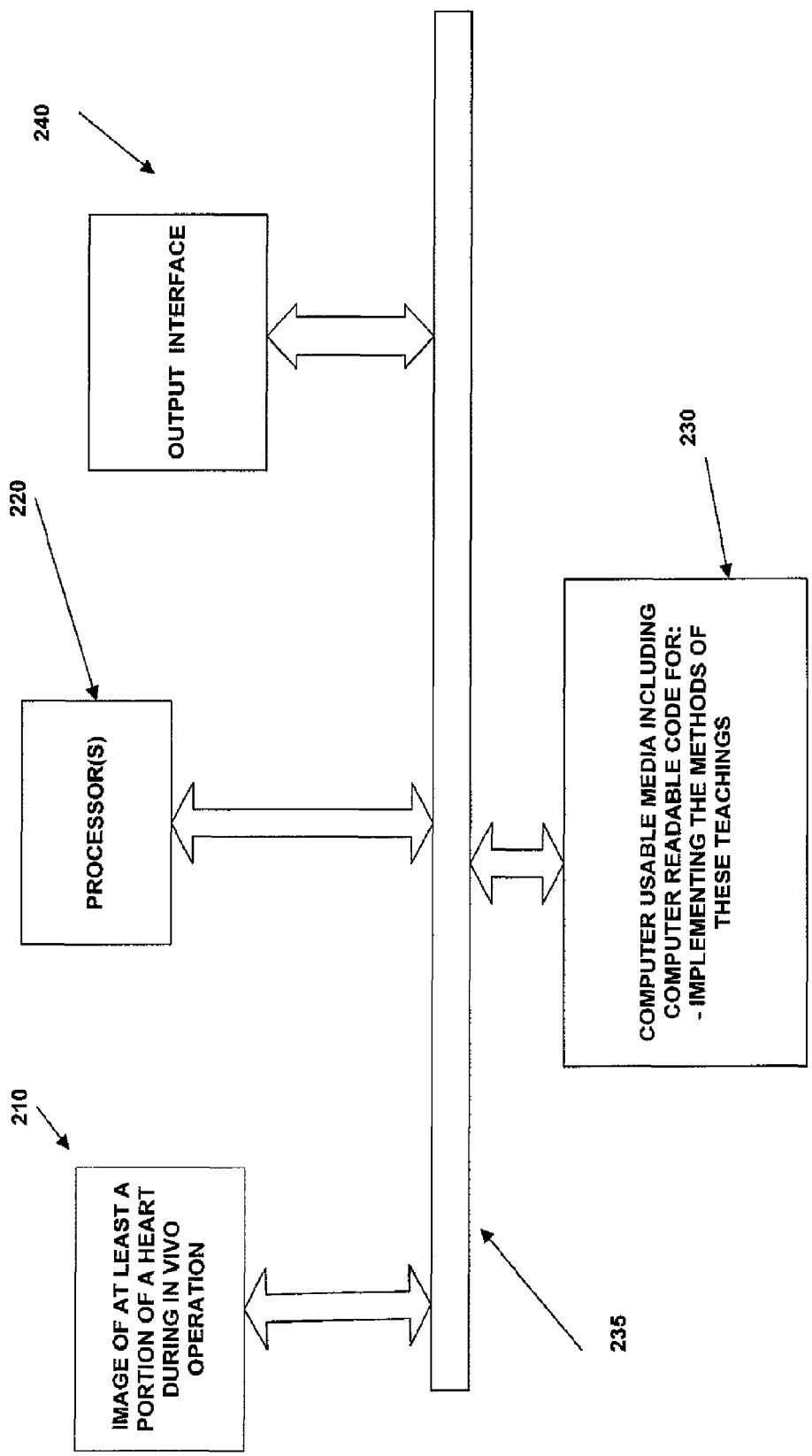
FIG. 3 is a schematic block diagram representation of an embodiment of the system of these teachings.

FIG. 3 shows a block diagram representation of an embodiment of the system of these teachings. The embodiment of the system of these teachings shown in FIG. 3 includes one or more processors 220 and one or more computer usable media 230 that has computer readable code embodied therein, the computer readable code causing the one or more processors to obtain, from an image 210 of at least a portion of a heart during in vivo or in vitro operation, tissue displacement information, and obtaining, from the tissue displacement information, stresses caused in the tissue displacements, whereby information on the action potential(s) inducing the stresses can be obtained. The information on the action potentials can be provided through an output interface 240. The image information 210, the one or more processors 220, the computer usable media 230 and the output interface 240 are operatively connected by an interconnection component 235 (for example, a computer bus). In another embodiment, the computer readable code causes the one or more processors to determine fiber orientation within planes of cardiac fibers.

As part of the process used to test the inverse model algorithm, a forward model was developed. The forward model simulates the biomechanical response of the 3-D cardiac tissue to a given time-dependent active stress field meant to represent the stress created by a propagating action potential.

Both forward and inverse models are based on the following equations:

$$\frac{\partial}{\partial X_M}\left[(T_{MN}(E) + T_{MN}^{active} - pC_{MN}^{-1})\frac{\partial x_j}{\partial X_N}\right] = 0 \text{ and} \quad (1)$$

$$\det(F) = 1 \quad (2)$$

Here $X_N$ and $x_j$ (N,j=1, 2, 3), are the coordinates in the undeformed and deformed coordinate systems, respectively, $T_{MN}(E)$ is the passive second Piola-Kirchhoff stress tensor, which depends on the strain tensor $E \equiv \frac{1}{2}(C-I)$ where $C \equiv F^T F$ and $F_{jM} = \partial x_j/\partial X_M$, p is the local hydrostatic pressure, and $T_{MN}^{active}$ is the stress tensor due to the action potential induced force generated parallel to the orientation of the myocardial fibers. Sums over repeated indices are implicit. Equation (1) is a statement of force balance and ignores inertia, which is appropriate for the timescales being considered. The myocardium is also considered as an elastic medium. (While the myocardium is perhaps more likely to be pseudoelastic, the variations of the stretch ratios (strains) for any given stress are no more than 20%). For the function $T_{MN}(E)$, the orthotropic pole-zero model of Nash and Hunter was used (Nash M P, Hunter P J, Computational Mechanics of the heart, J Elasticity, 2000; 61:113-141, incorporated by reference herein in its entirety for all purposes). Equation (2) together with the appearance of the hydrostatic pressure in Eq. (1) expresses the assumption of incompressibility, common in the study of cardiac biomechanics.

In some instances, it is expedient to use the linearized version of these equations, $$\frac{\partial}{\partial X_M}\left[\frac{1}{2}\frac{\partial T_{MN}}{\partial E_{PQ}}(0)\left(\frac{\partial \delta x_P}{\partial X_Q} + \frac{\partial \delta x_Q}{\partial X_P}\right) + T_{MN}^{active} - p\delta_{MN}\right] = 0 \text{ and} \quad (3)$$

$$\frac{\partial \delta x_M}{\partial X_M} = 0 \quad (4)$$

where, $T_{MN}^{active}$, p and the displacements $\delta x_p \equiv x_p - x_p$ are assumed small (i.e., $O(\epsilon)$, where $\epsilon$ is a small number). This approximation should also be valid in the study of ventricular fibrillation when the tissue deformations are typically very small; however for cases of sinus rhythm or external electrical pacing, the fully nonlinear equations (1) and (2) will be used.

Finite element versions of Eqs. (3) and (4) were generated for the case of a tissue whose undeformed shape was that of a three-dimensional rectangular solid. Rectangular elements were defined in the obvious way relative to a 3-d rectangular lattice of nodes whose edges coincided with the edges of the undeformed tissue. The spacings between nodal points, denoted $\Delta X$, $\Delta Y$, and $\Delta Z$, were chosen to be uniform in each direction. The values of these spacings may be arbitrarily chosen, as nothing in the resulting equations depends on their values. For this initial study, a relatively small, 10×10×10 lattice of nodes was employed. Weighting functions for Eqs. (3) took the form $N_l(X)=\Sigma_e N_l^e(X)$, for a given node l, where the sum is over adjacent elements e and $X \equiv (X_1, X_2, X_3) \equiv (X, Y, Z)$. The element shape function $N_l^e(X)$ is defined as $N_l^e(X)=XYZ/\Delta X \Delta Y \Delta Z$ when the node l is located at $(\Delta X, \Delta Y, \Delta Z)$ and the element e is $[0,\Delta X] \times [0,\Delta Y] \times [0,\Delta Z]$, with all other element shape functions defined in analogous fashion. The displacements were defined using trial functions identical to these weighting functions; i.e., $\delta x_p(X) = \delta x_p^l N_l(X)$, where the $\delta x_p^l$'s are constants. In contrast, since p, $T_{MN}^{active}$, and $\partial T_{MN}(0)/\partial E_{PQ}$ appear in Eq. (3) with one less derivative than the displacements, it is appropriate to define them in terms of amplitudes defined on the elements rather than the nodes; e.g., $p(X) = p^e \overline{N}_e(X)$, etc. In that case, a lower order trial function is used, defined simply as $\overline{N}_e(X)=1$ for X within the element e, and 0 otherwise. This lower order function was also used as the weighting function for Eq. (4). When these finite element representations were substituted into Eqs. (3) and (4), multiplied by the weighting functions, integrated over X, the following is obtained:

$$\frac{1}{2}\left[\left(\frac{\partial T_{MN}}{\partial E_{PQ}}(0)\right)^f + \left(\frac{\partial T_{MN}}{\partial E_{QP}}(0)\right)^f\right]\left(\int \frac{\partial N_j}{\partial X_M}\overline{N}_f\frac{\partial N_l}{\partial X_Q}dX\right)\delta x_P^j + \quad (5)$$
$$\left(\int \frac{\partial N_j}{\partial X_M}\overline{N}_e dX\right)U_{M1}^e U_{N1}^e (t^{active})^e - \left(\int \frac{\partial N_j}{\partial X_N}\overline{N}_e dX\right)p^e = 0$$

$$\left(\int \overline{N}_e \frac{\partial N_l}{\partial X_P}dX\right)\delta x_P^l = 0 \quad (6)$$

Integration by parts was performed in deriving Eq. (5), utilizing homogeneous Neumann boundary conditions (i.e., force-free conditions on all the surfaces. The active stress tensor used has only one nonzero component, $t^{active}$, in the 1-1 direction, before rotation by a unitary matrix U orients the tensor in the local fiber direction. This corresponds to the active contraction due to the passage of an action potential occurring in the fiber direction, which is defined to be in the "1" direction before rotation. Sums over e and f are over elements (only a single sum in the middle term), sums over l are over nodes, and sums over M, P and Q are over 1, 2 and 3. Equation (5) depends on N=1, 2, 3 and node index j; Eq. (6) just depends on e. Equations (5) and (6) are linear and homogeneous in the displacements defined at the nodes, $\delta x_p^l$, the active tensions along the local fiber direction in each of the elements, $(t^{active})^e$, and the pressures in the elements, $p^e$. Any arbitrary rigid rotation or translation of a solution to Eqs. (5) and (6) is again a solution; thus it was useful to constrain the solution to a particular translation and rotational orientation by adding six equations to Eqs. (5) and (6): three that hold the mean displacement of the nodes to 0 in all three dimensions (which also translates into no net displacement of the center of mass in the case of substantially uniform mass density):

$$\sum_l \delta x_P^l = 0 \quad (7)$$

and three equations that prevent rotation around the center of mass:

$$\sum_l (X_l - X^{cm}) \times \delta x^l = 0 \qquad (8)$$

where $$X^{cm} \equiv \sum_l X_l.$$

The equations therefore have the form, $$\begin{vmatrix} A_1 & B_1 & C_1 & D_1 & E_1 \\ A_2 & B_2 & C_2 & D_2 & E_2 \\ A_3 & B_3 & C_3 & D_3 & E_3 \\ A_4 & B_4 & C_4 & 0 & 0 \\ a_5 & b_5 & c_5 & 0 & 0 \end{vmatrix} \begin{bmatrix} \delta x_1 \\ \delta x_2 \\ \delta x_3 \\ p \\ t^{active} \end{bmatrix} = 0 \qquad (9)$$

where all the elements in the first "super" matrix on the left are themselves matrices, and all the elements of the second matrix are column vectors. The first three row of the matrix on the left of Eq. (9) correspond to the three components of Eq. (5), the fourth row corresponds to Eq. (6), and the fifth row imposes the constraints defined by Eqs. (7) and (8). The above is an exemplary instance where the determination of stresses for each pixel or nodal point in a group of pixels or nodal points is obtained by operating on displacements for each pixel or nodal point in a group of pixels or nodal points rather than by operating on each pixel or nodal point separately.

For the function governing the passive tension $T_{MN}(E_{PQ})$, the "pole-zero" formulation, described by Nash to be appropriate for the mechanics of cardiac muscle, is utilized. The formulation describes the tissue as an orthotropic hyperelastic medium.

The "Forward" Model:
Determination of the tissue displacements caused by a given active stress field. This function is easily accomplished by rewriting Eq. (9) as, $$\begin{vmatrix} A_1 & B_1 & C_1 & D_1 \\ A_2 & B_2 & C_2 & D_2 \\ A_3 & B_3 & C_3 & D_3 \\ A_4 & B_4 & C_4 & 0 \\ a_5 & b_5 & c_5 & 0 \end{vmatrix} \begin{bmatrix} \delta x_1 \\ \delta x_2 \\ \delta x_3 \\ p \end{bmatrix} = \begin{bmatrix} -E_1 \\ -E_2 \\ -E_3 \\ 0 \\ 0 \end{bmatrix} [t^{active}] \qquad (10)$$

Given values for all the active stresses in the column vector $t^{active}$, there are four sets of equations (i.e., those associated with the first four rows of the matrix on the left) for the four unknown column vectors $\delta x_1$, $\delta x_2$, $\delta x_3$ and p. These four sets of equations, when combined with the 6 constraints defined by the fifth row, have sufficient rank to allow solution using a sparse matrix equation solver, such as but not limited to, the built-in sparse matrix equation solver in the Matlab programming environment (The Mathworks, Inc.), thus yielding a complete description of the tissue deformation and compensating hydrostatic pressure produced by a given active stress field. Since there are no time derivatives in these equations, the frames of a movie displaying the deformations induced by a time-dependent active stress field may be created simply by solving Eq. (10) repeatedly for each time for which there is active stress field data.

The Inverse Model:
Determination of the active stresses produced by action potentials using tissue displacement data. Two variants of the inverse model were utilized. Variant 1: If two of the three direction components of the displacements can be extracted from the full three-dimensional volume, the model can reconstruct the active stress field that caused the displacements everywhere within the volume. The appropriate form of Eq. (9) for this method is, $$\begin{vmatrix} B_1 & D_1 & E_1 \\ B_2 & D_2 & E_2 \\ B_3 & D_3 & E_3 \\ B_4 & 0 & 0 \\ b_5 & 0 & 0 \end{vmatrix} \begin{bmatrix} \delta x_2 \\ p \\ t^{active} \end{bmatrix} = \begin{vmatrix} -A_1 & -C_1 \\ -A_2 & -C_2 \\ -A_3 & -C_3 \\ -A_4 & -C_4 \\ -a_5 & -c_5 \end{vmatrix} \begin{bmatrix} \delta x_1 \\ \delta x_3 \end{bmatrix} \qquad (11)$$

In this case, the four sets of equations plus the 6 constraints represented by Eq. (11) actually constitute an overdetermined problem for the three unknown fields, $\delta x_2$, p and $t^{active}$. The set of unknown fields are therefore solved for in the least-squares sense, in one instance, using Matlab's built-in sparse matrix solvers.

Variant 2: If the deformation data come from a two-dimensional imaging plane, say, a plane oriented in the $x_1$ and $x_3$ (i.e., the x and z) directions, embedded within the volume, and consist of the two in-plane directional components of the displacement, within the same plane, the active stress field that caused it can be estimated. The solution to this problem is relevant to the two-dimensional ultrasound imaging techniques that is currently being used experimentally. In this case, however, there is technically not enough data to uniquely determine the stress field. The problem is that the spatial derivatives in the direction perpendicular to the plane contribute to the determination of the stress. These derivatives cannot be determined solely from displacement data obtained from the plane. One of these derivatives may be obtained from the incompressibility condition; i.e., $\partial \delta x_2/\partial X_2 = -\partial \delta x_1/\partial X_1 - \partial \delta x_3/\partial X_3$; however this still leaves the other two normal derivatives, $\partial \delta x_1/\partial X_2$ and $\partial \delta x_3/\partial X_2$ undetermined. This can be overcome if all planes parallel to this plane contain identical data for the displacement fields $\delta x_1$ and $\delta x_3$. Then, Eq. (11) is applied. This condition is valid so long as the variation of mechanical deformation is small in the $x_2$ (i.e., the y) direction.

As with the forward problem, either inverse model can generate frames for a movie illustrating the motion of the active stress field by simply solving Eq. (11) for each time for which displacement data are available.

The fact that the system of equations describing the inverse problem is overdetermined also enables embodiments in which other quantities may be solved for. In one embodiment, the angle describing fiber orientation within the planes of fibers that typically lay parallel to the myocardial surfaces is obtained. These angles appear in Eq. (7) through the matrix elements' dependence on them. That embodiment eliminates the necessity of determining the fiber angles experimentally, which obviously makes the method of these teachings much more attractive as an imaging modality.

To illustrate the methods of these teachings, the "forward" model based on Eq. (10) was used to generate mechanical deformations of a cubic block of tissue shown FIG. 4(b) as the response to a traveling plane wave of active stresses (FIG. 4(a)) oriented along the local fiber direction. This plane wave is meant to behave as the contractile force that would be produced by an action potential plane wave. The block of tissue contained fibers whose direction rotated with depth, as is also the case in actual myocardial tissue. The fibers were oriented in the y-direction on the top surface of the cube-shaped tissue in FIG. 4(b), rotated in the clockwise direction as a linear function of z to point in the x-direction in the horizontal plane in the middle of the cube, and continued to rotate clockwise so that they pointed back in the y-direction at the bottom of the cube.

Figures 4A, 4B, 4C, 4D, 4E, 4F, 4G, 4H, 4I, 4J:
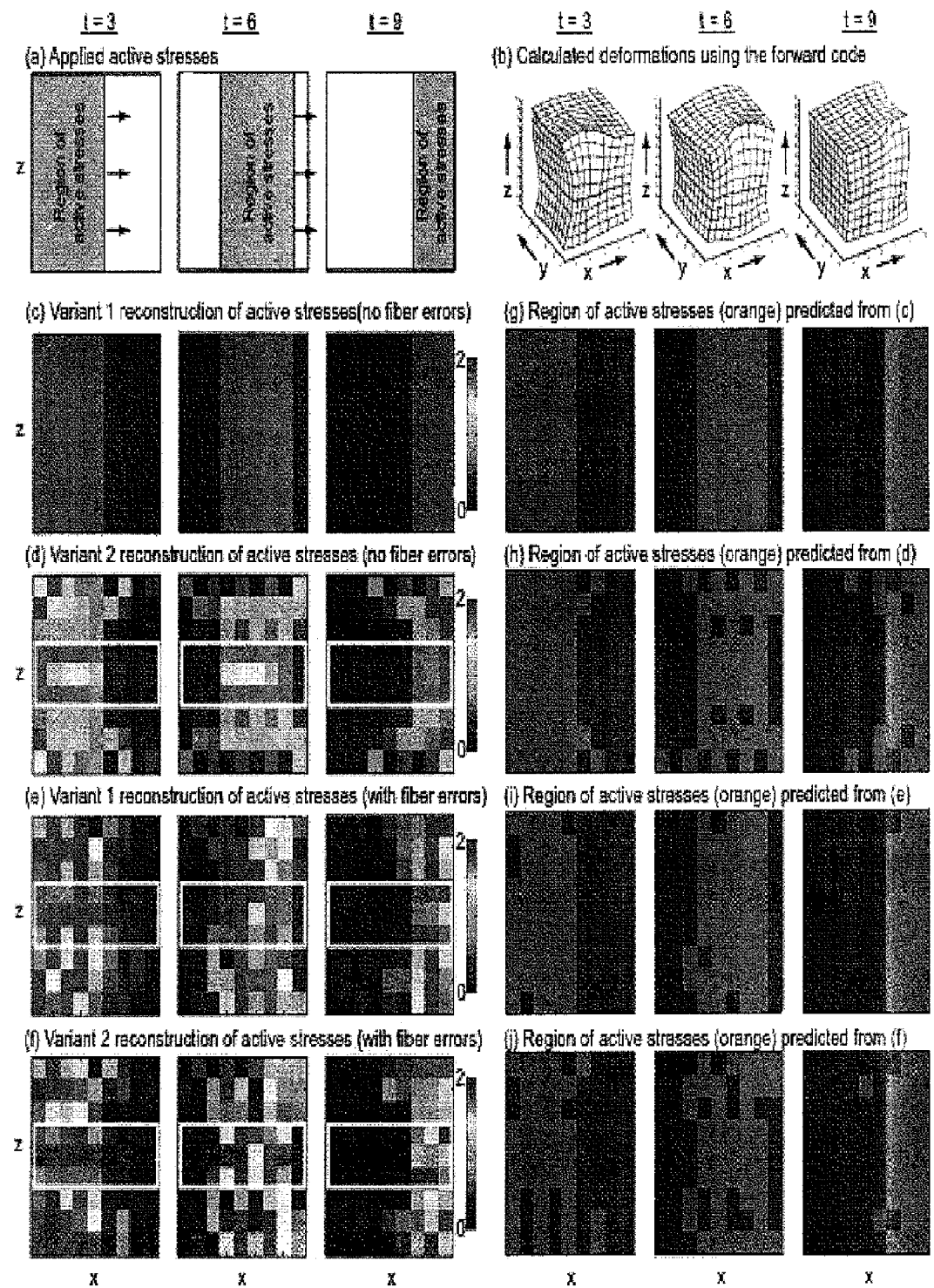
FIGS. 4a-4j show the input into, and the results from, the forward model, respectively.

The deformations obtained from the forward model are used as input into the two variants of the "inverse" model, based on Eq. (11). Variant 1, which takes as input two of the three displacement components expressed as spatially 3-D data, was able to reproduce the original active stresses essentially exactly, as is readily apparent by comparing FIGS. 4(c) to 4(a). Variant 2 was able to do a fair job of reconstructing the stress field plane wave in the plane from which the deformation data were taken (FIG. 4(d)), When random errors were purposely introduced into the fiber direction, both variants of the inverse code was still able to recreate the active stresses fairly well, as illustrated in FIGS. 4(e) and (f), suggesting that the reconstruction process is not highly sensitive to errors in measuring the fiber direction in the experiment. Here the errors were chosen from a distribution of zero mean and standard deviation of 10°. For these last three cases (Variant 2 without fiber errors and both variants with fiber errors), the reconstruction was more accurate in the region containing fibers oriented parallel or nearly parallel to the x-axis. The intersection of these regions with the displayed cross section is shown as a white rectangle in each of the panels of FIGS. 4(d-f). The higher accuracy in these rectangles is manifested as a closer agreement the between the calculated active stresses appearing in these rectangles and those appearing in the analogous region of FIG. 4(a) than was obtained outside these rectangles.

Studies of this type were conducted for 10 different orientations of this rotated fiber pattern. Specifically, the ability of Variants 1 and 2 to reconstruct the active stress field of a plane wave propagating in the x-direction, in both the presence and absence of fiber direction error, was studied for the cases in which the entire fiber orientation spatial pattern just described had been rotated through angles ranging from 0° to 90° around the z axis in increments of 10°. For all 10 orientations, Variant 1 without fiber error reproduced the original active stress field to within 1 part in $10^{-12}$. For the other three cases (i.e., Variant 2 without fiber errors and both variants with fiber errors), the reconstruction was more accurate in regions in which the fiber orientations lie in the x-z plane. For example, for the fiber orientation pattern used in all the plots in FIG. 4, this region intersects the displayed cross-section in the white rectangle each panel of FIGS. 4(d-f). The higher accuracy within each rectangle is manifested as a closer agreement the between the calculated active stresses appearing in these rectangles and those appearing in the analogous region of FIG. 4(a) than was obtained outside these rectangles. The relative position of this rectangle changes in each of the 10 orientations, but in each case, the accuracy was found to be higher within the rectangle. Other than differences in the positioning of this higher accuracy region, the reconstructed active stresses for the 10 cases did not exhibit features substantively different from those shown in FIG. 4(c-f).

Figures 5A, 5B, 5C, 5D:
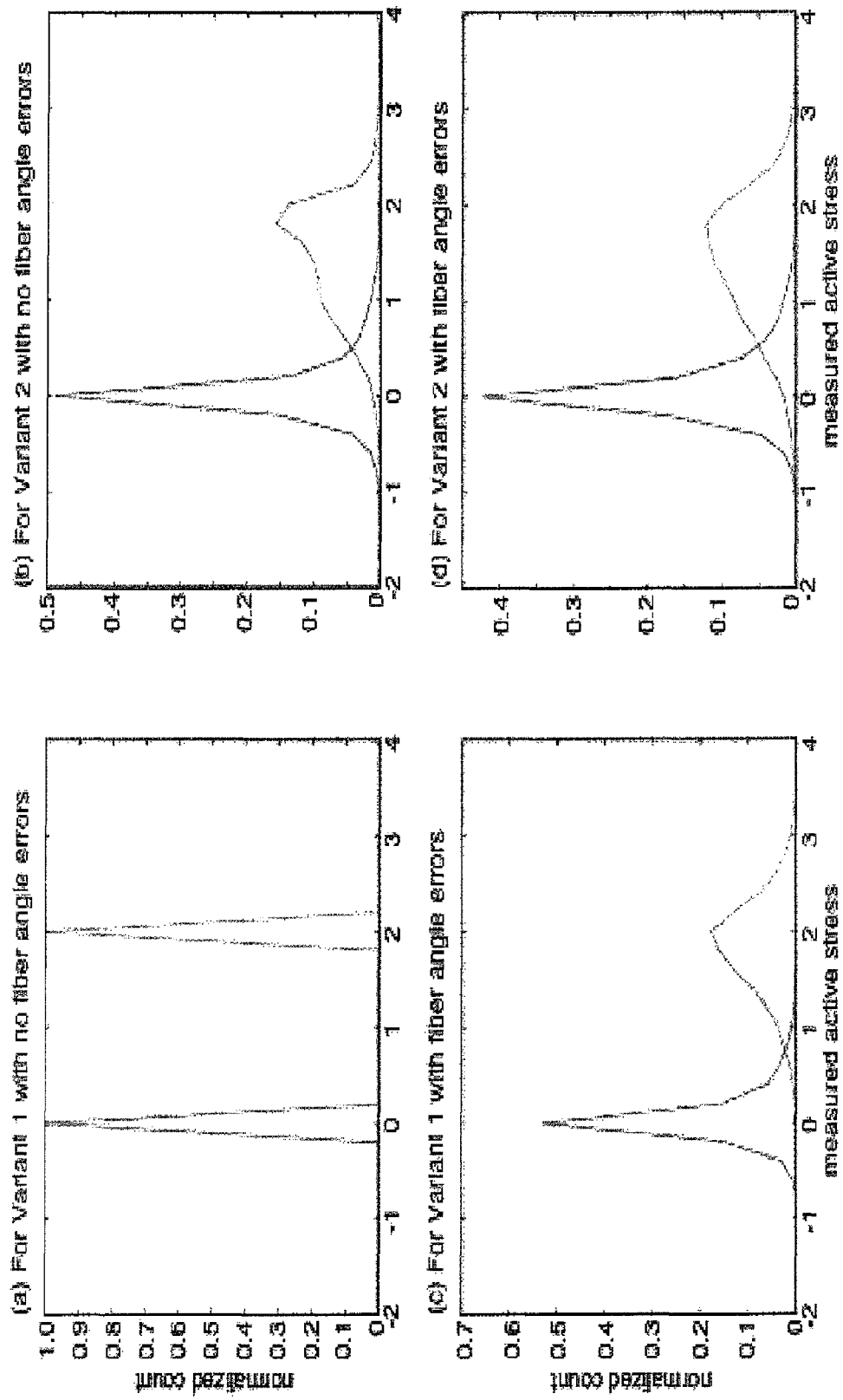
FIGS. 5a-5d show the results obtained when the magnitudes of the reconstructed active stresses of all the cells inside and outside the original non-zero active stress regions at all measured times from all 10 of these studies are plotted as distributions.

When the magnitudes of the reconstructed active stresses of all the cells inside (red) and outside (blue) the original non-zero active stress regions at all measured times from all 10 of these studies were plotted as distributions, the plots shown in FIG. 5 were obtained. As expected, for Variant 1 with no fiber orientation errors, there is no spread of the values around the original values of 2.0 and 0.0 respectively. (The slight amount of spread shown in FIG. 5(a) is entirely due to the width of the bins used to create the distributions.) The distributions for the other three cases showed substantial spread, with somewhat more spread exhibited by the cells inside the original non-zero active stress region for the Variant 2 cases (FIGS. 5(b) and (d)) than the Variant 1 case (FIG. 5(c)). Despite this spread, the two distributions are substantially well separated from each other.

When two-dimensional ultrasound imaging is utilized, the two components of displacement are only known within a two-dimensional imaging plane, a slow variation of the two in-plane displacements in the perpendicular direction may be necessary. When a slow variation of the two in-plane displacements in the perpendicular direction is presumed, the method of these teachings is still able to substantially reconstruct a propagating plane wave consisting of active stresses oriented along the local fiber direction.

A fully 3D ultrasound imaging system appropriate for the imaging modality of these teachings is achievable. Three-dimensional ultrasound probes were originally proposed in 1990 by Von Ramm and Smith and the technology has since advanced to the point where real-time images of the heart can be taken as rapidly as 33 ms per slice. Existing 3D ultrasound equipment may be adequate for use with the present teachings, and may only require modifications to the software.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, punched cards, paper tape, any other physical medium with patterns of holes, a RAM, a PROM, and EPROM, a FLASH-EPROM, any other memory chip or cartridge. As stated in the USPTO 2005 Interim Guidelines for Examination of Patent Applications for Patent Subject Matter Eligibility, 1300 *Off. Gaz. Pat. Office* 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although the teachings have been described with respect to various embodiments, it should be realized these teachings are also capable of a wide variety of further and other embodiments within the spirit and scope of the appended claims.

What is claimed is:

1. A method for sensing cardiac activity, the method comprising:
   obtaining an image of at least a portion of a heart during operation;
   obtaining, from the image, tissue displacement information;
   obtaining, from the tissue displacement information, stresses causing the tissue displacements; wherein obtaining the stresses further comprises obtaining the stresses by utilizing an inverse model; and
   determining fiber orientation within planes of cardiac fibers;
   whereby information on action potentials inducing the stresses can be obtained.

2. The method of claim 1 wherein the step of obtaining the image comprises the step of obtaining an ultrasound image.

3. The method of claim 2 wherein the step of comprising the ultrasound image comprises the step of obtaining a brightness (B) ultrasound image.

4. The method of claim 1 wherein the step of obtaining an image of at least a portion of a heart during operation it comprises the step of obtaining an image of at least a portion of the heart during in vivo/in vitro operation.

5. A system for sensing cardiac activity, the system comprising:
   at least one processor; and
   at least one computer usable medium having computer readable code embodied therein, said computer readable code causing said at least one processor to:
      obtain, from an image of at least a portion of a heart during operation, tissue displacement information;
      obtain, from the tissue displacement information, stresses causing the tissue displacements; the stresses being obtained by utilizing an inverse model; and
      determine fiber orientation within planes of cardiac fibers;
   whereby information on action potentials inducing the stresses can be obtained.

6. The system of claim 5 wherein the image is an ultrasound image.

7. The system of claim 6 wherein the ultrasound image is a brightness (B) ultrasound image.

8. The system of claim 5 wherein the computer readable code, in causing said at least one processor to obtain an image, causes said at least one processor to obtain an image of at least a portion of the heart during in vivo/in vitro operation.

9. A computer program product comprising a non-transitory computer readable storage medium having computer readable code embodied therein for causing a computer system to:
   obtain, from an image of at least a portion of a heart during operation, tissue displacement information;
   obtain, from the tissue displacement information, stresses causing the tissue displacements; the stresses being obtained by utilizing an inverse model; and
   determine fiber orientation within planes of cardiac fibers;
   whereby information on action potentials inducing the stresses can be obtained.

10. The computer program product of claim 9 wherein the image is an ultrasound image.

11. The computer program product of claim 9 wherein the ultrasound image is a brightness (B) ultrasound image.

12. The computer program product of claim 9 wherein the computer readable code, in causing said computer system to obtain an image, causes said computer system to obtain an image of at least a portion of the heart during in vivo/in vitro operation.

* * * * *